(12) United States Patent
Fujii et al.

(10) Patent No.: US 8,074,799 B2
(45) Date of Patent: Dec. 13, 2011

(54) HOLDING TRAY

(75) Inventors: Naoto Fujii, Itabashi-ku (JP); Yusuke Ishikawa, Itabashi-ku (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 12/961,915

(22) Filed: Dec. 7, 2010

(65) Prior Publication Data

US 2011/0139651 A1    Jun. 16, 2011

(30) Foreign Application Priority Data

Dec. 14, 2009  (JP) ................................ 2009-282803

(51) Int. Cl.
*B65D 85/20* (2006.01)

(52) U.S. Cl. ............ 206/379; 206/369; 211/69; 433/79; 422/300

(58) Field of Classification Search .................. 206/379, 206/369, 370, 439, 443, 562; 211/69; 433/77, 433/79; 422/300, 297

See application file for complete search history.

(56) References Cited

U.S. PATENT DOCUMENTS

| | | | | |
|---|---|---|---|---|
| 1,451,806 | A * | 4/1923 | Baldridge | 206/369 |
| 3,270,416 | A * | 9/1966 | Massa | 433/77 |
| 5,525,314 | A * | 6/1996 | Hurson | 422/300 |
| 6,328,565 | B1 | 12/2001 | Rose | |
| 6,474,481 | B1 * | 11/2002 | Liu | 211/69 |
| 7,401,700 | B2 * | 7/2008 | Dost et al. | 206/379 |
| 7,896,158 | B2 * | 3/2011 | Taylor | 206/377 |
| 2004/0069668 | A1 * | 4/2004 | Finnigan | 206/372 |
| 2007/0104609 | A1 * | 5/2007 | Powell | 422/1 |
| 2009/0266728 | A1 | 10/2009 | Turner et al. | |
| 2010/0028828 | A1 * | 2/2010 | Vogel et al. | 433/77 |

FOREIGN PATENT DOCUMENTS

| | | |
|---|---|---|
| DE | 20 2007 004 638 U1 | 6/2007 |
| FR | 1024588 A | 4/1953 |
| GB | 2329 337 A | 3/1999 |
| JP | 2008-526298 T | 7/2008 |
| WO | WO 2006/071180 A1 | 7/2006 |

OTHER PUBLICATIONS

European Search Report in English issued Mar. 22, 2011 in European Patent Application No. 10015483.0.

* cited by examiner

*Primary Examiner* — David Fidei
(74) *Attorney, Agent, or Firm* — Oblon, Spivak, McClelland, Maier & Neustadt, L.L.P.

(57) ABSTRACT

For easy washing and sterilizing of a holding tray for drill bits used in a dental implant operation, a holding tray X includes a tray main body 1 made of a hard material capable of autoclave sterilizing and holding members 2 made of an elastic material capable of autoclave sterilizing, the tray main body 1 includes holding plates 1b and holding member supporting plates 1c on a back surface of a substrate part 1a having rows of linearly aligned through holes 1aa for drill bits, the holding plates 1b include half circular cylindrical recessed parts 1ba at portions corresponding to the through holes 1aa, the supporting plates 1c have a fixed interval to a plane 1bb along the recessed part 1ba, and the holding members 2 are detachably held between the holding plates 1b and the supporting plates 1c to hold the drill bits together with the recessed parts 1ba.

3 Claims, 4 Drawing Sheets

HOLDING TRAY

BACKGROUND OF THE INVENTION

1. Field of the Invention

The present invention relates to a holding tray for inserting and holding a plurality of drill bits and instruments other than the drill bits, which are used for every patient at a time of performing drilling of an embedding hole for a dental implant fixture and following operations after the drilling.

2. Description of the Conventional Art

In recent years, as a treatment method for recovering the lost oral cavity function of a lost tooth part, an implant treatment has been greatly used. In the implant treatment, a dental prosthesis is fixed on the oral cavity inner side of a dental implant fixture, which is embedded in a jawbone of the lost tooth part, is bone-bonded to the jawbone, and comes to be an artificial tooth root.

In the implant treatment, drilling of an embedding hole for a dental implant fixture and following operations after the drilling are performed by steps of incising or removing a gingiva to expose a jawbone of a lost tooth part; forming the embedding hole in the jawbone of the lost tooth part by using drill bits, such as guide drill bits, depth drill bits, pilot drill bits, twist drill bits, counter bore drill bits, and bone taps, direction indicators, and the like; embedding a dental implant fixture having a proper size into the embedding hole by using a fixture driver; and covering the oral cavity inner side of the embedded dental implant fixture with a cover screw by using a skill driver.

Accordingly, when the drilling of the embedding hole for a dental implant fixture and the following operations after the drilling are performed, a plurality of drill bits and instruments other than the drill bits are used. Thus, in order to make an operator's operation during a treatment easy, these drill bits and instruments other than the drill bits are inserted and held in a holding tray having a plurality of through holes provided therein.

For example, Japanese Translation of PCT Publication No. 2008-526298 discusses such a holding tray. In this holding tray, a rubber grommet having a center hole is fitted to each of the plurality of through holes provided in a tray substrate, to thereby insert and hold each of the drill bits and the instruments other than the drill bits in each through hole. Further, each of the drill bits and each of the instruments other than the drill bits can be easily taken out from each through hole when using the drill bits and the instruments. However, in this holding tray, since each of the drill bits and the instruments other than the drill bits is returned to the holding tray together with blood and the like which adhere during an operation, it is necessary that the rubber grommets fitted to each of the through holes are taken out one by one, washed together with the tray substrate, re-fitted to each of the through holes, and subjected to an autoclave sterilizing treatment. Therefore, since it takes time and efforts for the washing and sterilizing treatments, there is a problem that an enormous burden is put on the operator.

SUMMARY OF THE INVENTION

Problem to be Solved by the Invention

An objective of the present invention is to provide a holding tray capable of inserting and holding drill bits and instruments other than the drill bits, which are used for every patient at a time of performing drilling of an embedding hole for a dental implant fixture and following operations after the drilling, in a state of easily taking out those, and capable of easy washing and sterilizing treatment operations after use.

Means for Solving the Problem

Present inventors carried out earnest works to solve the aforementioned problems, and as a result, they found out the followings to complete the present invention. A holding tray for inserting and holding a plurality of drill bits and instruments other than the drill bits, which are used for every patient at a time of performing drilling of an embedding hole for a dental implant fixture and following operations after the drilling, is configured to include a tray main body made of a hard material capable of autoclave sterilizing and holding members made of an elastic material capable of autoclave sterilizing. The tray main body includes holding plates and holding member supporting plates on a back surface of a substrate part. The substrate part has a plurality of hole rows consisting of a plurality of linearly aligned through holes in which each of the drill bits and instruments other than the drill bits are inserted. The holding plates are erected along the hole rows, have a flat plate shape, and have half circular cylindrical recessed parts at portions corresponding to each of the through holes. The holding member supporting plates are erected respectively having a fixed interval with respect to a plane along the half circular cylindrical recessed part side of the holding plate. The holding members are detachably clamped and attached between the holding plates and the holding member supporting plates, and clamp and hold the drill bits and the instruments other than the drill bits inserted into the through holes in the hole rows, together with the half circular cylindrical recessed parts of the holding plates. According to this holding tray, the drill bits and the instruments other than the drill bits, which are inserted into the through holes respectively, are held by the half circular cylindrical recessed parts of the holding plates and the holding members. Thus, these drill bits and the instruments other than the drill bits can be inserted and held in a state of being easily taken out at a time of using those. Further, a rubber grommet is not fitted to each through hole, but the holding members are detachably held and attached between the holding plates erected along the hole rows and the holding member supporting plates. Furthermore, the tray main body and the holding members are made of the materials capable of autoclave sterilizing. Thus, after using the holding tray, the holding members and the tray main body can be easily washed by only taking out the holding members from between the holding plates of the tray main body and the holding member supporting plates. Furthermore, an autoclave sterilizing treatment can be performed by only attaching the holding members between the holding plates of the tray main body and the holding member supporting plates after the washing operation.

According to an aspect of the present invention, a holding tray for inserting and holding a plurality of drill bits and instruments other than the drill bits used for every patient at a time of drilling of an embedding hole for a dental implant fixture and following operations after the drilling, includes a tray main body made of a hard material capable of autoclave sterilizing and holding members made of an elastic material capable of autoclave sterilizing. The tray main body includes holding plates and holding member supporting plates on a back surface of a substrate part having a plurality of hole rows consisting of a plurality of linearly aligned through holes in which each of the drill bits and instruments other than the drill bits are inserted. The holding plates are erected along the hole rows, have a flat plate shape, and include half circular cylindrical recessed parts at portions corresponding to each of the through holes. The holding member supporting plates are erected respectively having a fixed interval with respect to a plane along the half circular cylindrical recessed part side of the holding plate. The holding members are detachably clamped and attached between the holding plates and the holding member supporting plates, and clamp and hold the drill bits and the instruments other than the drill bits inserted into the through holes in the hole rows, together with the half circular cylindrical recessed parts of the holding plates.

Further, if a display part for displaying an order to use the drill bits is provided on a surface of the substrate part of the tray main body, an operator can select a drill bit to be used according to the order displayed on the display part, so that it is preferable.

Furthermore, if a section display part for sectioning and displaying locations in which the instruments other than the drill bits are inserted is provided on the surface of the substrate part of the tray main body, the operator can select the instruments other than the drill bits at a glance, so that it is preferable.

EFFECT OF THE INVENTION

According to the holding tray of the present invention, the drill bits and the instruments other than the drill bits, which are inserted into the through holes respectively, are clamped and held by the half circular cylindrical recessed parts of the holding plates and the holding members. Thus, these drill bits and the instruments other than the drill bits can be inserted and held in a state of being easily taken out at a time of use. Further, a rubber grommet is not fitted to each through hole, but the holding members are detachably clamped and attached between the holding plates erected along the hole rows and the holding member supporting plates. Furthermore, the tray main body and the holding members are made of the materials capable of autoclave sterilizing. Thus, after using the holding tray, the holding members and the tray main body can be easily washed by only taking out the holding members from places between the holding plates of the tray main body and the holding member supporting plates. Furthermore, the autoclave sterilizing treatment can be performed by only attaching the holding members between the holding plates of the tray main body and the holding member supporting plates after the washing operation. Therefore, the washing and sterilizing treatment operations can be performed easily.

Further, if the display part for displaying an order to use the drill bits is provided on the surface of the substrate part of the tray main body, the operator can select a drill bit to be used according to the order displayed on the display part, so that it is preferable.

Furthermore, if the section display part for sectioning and displaying locations in which the instruments other than the drill bits are inserted is provided on the surface of the substrate part of the tray main body, the operator can select the instruments other than the drill bits at a glance, so that it is preferable.

DETAILED DESCRIPTION OF PREFERRED EMBODIMENT

A holding tray according to the present invention will be described in detail below with reference to the drawings.

Figure 9:
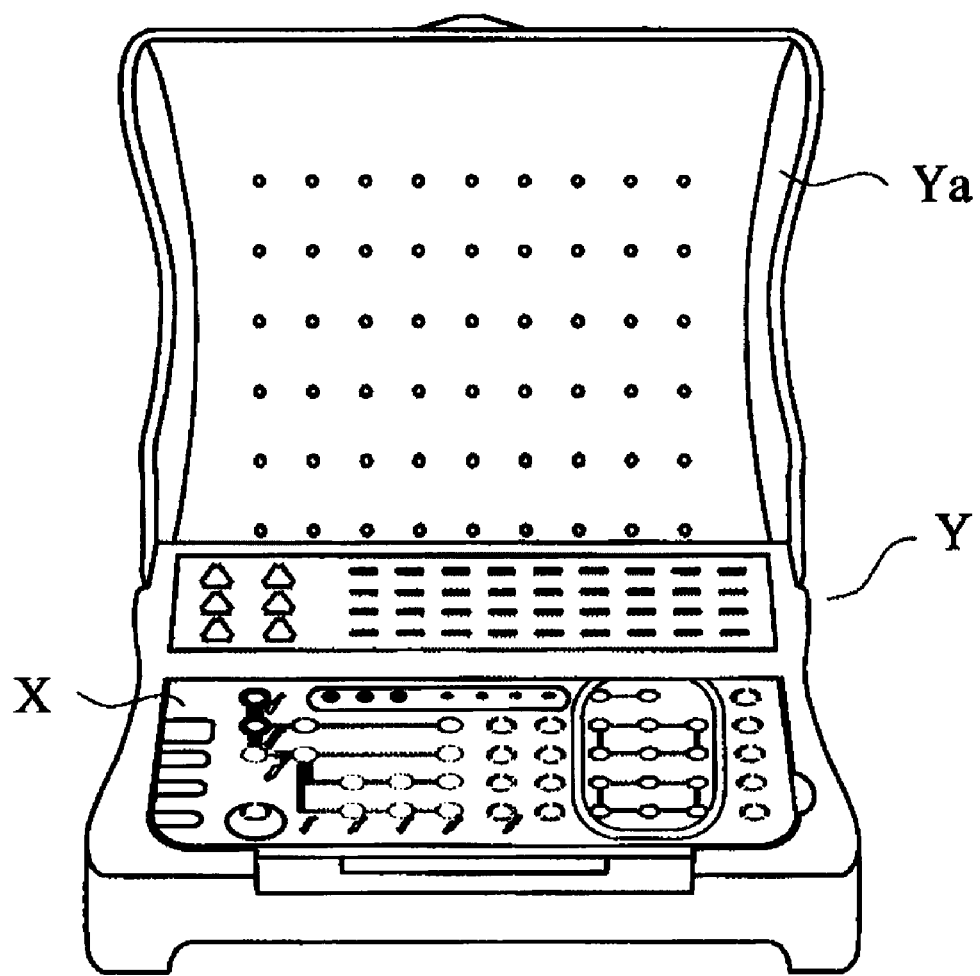
FIG. 9 is a view illustrating a state that the holding tray in FIG. 1 is housed in a housing case in a state of a cover being opened.

In the drawings, a holding tray X according to the present invention includes a tray main body 1 and a holding member 2. The holding tray X performs a function for inserting and holding a plurality of drill bits and instruments other than the drill bits which are used for every patient at a time of performing drilling of an embedding hole for a dental implant fixture and following operations after the drilling. As the drill bits inserted into the holding tray X, there are for example, guide drill bits, depth drill bits, pilot drill bits, twist drill bits, counter bore drill bits, and bone taps. Further, as the instruments other than the drill bits, there are for example, direction indicators, fixture drivers, cover screws, fixture drivers, and skill drivers. However, the drill bits and instruments other than the drill bits are not limited to the above if they can be inserted and held in the holding tray X. Furthermore, instruments used in a so-called second stage operation can be also inserted and held in the holding tray X. In addition, for example, as illustrated in FIG. 9, the holding tray X is housed in a housing case Y with a cover Ya made of a hard material capable of autoclave sterilizing, until it is used, is taken out from the housing case Y at a time of use, and is used.

The tray main body 1 includes a substrate part 1a, a holding plate 1b, and a holding member supporting plate 1c. The tray main body 1 is made of a hard member capable of autoclave sterilizing, so that the tray main body 1 can be subjected to the autoclave sterilizing treatment. As the hard member capable of autoclave sterilizing, plastics such as polypropylene, polyether sulfone, polyphenyl sulfone, and the like, or metals such as stainless steel and the like, can be used.

Figure 1:
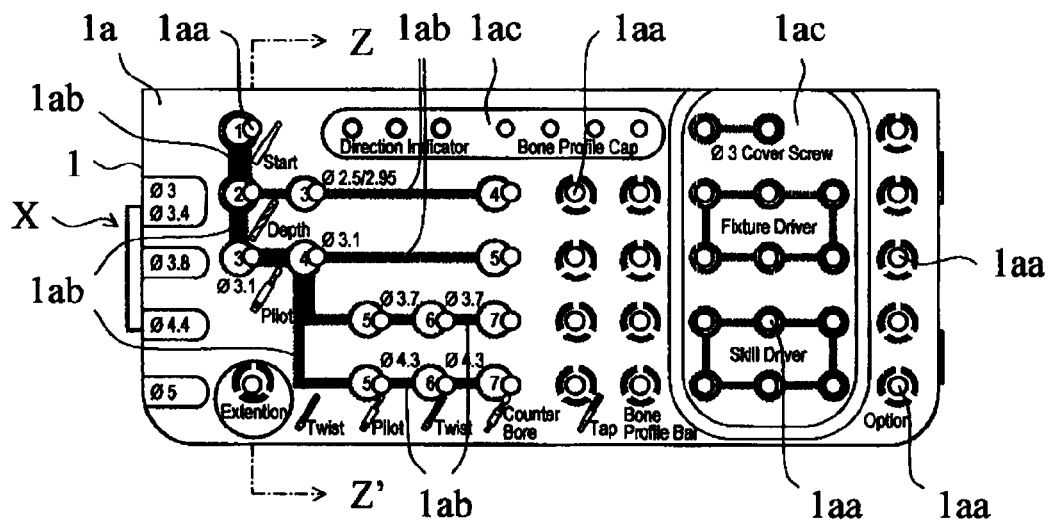
FIG. 1 is a plan view illustrating an example of a holding tray according to the present invention.

The substrate part 1a is a portion coming to be a base of the tray main body 1. The substrate part 1a has a plurality of through holes 1aa in which the drill bits and the instruments other than the drill bits are inserted respectively. In addition, in FIGS. 1, 2 and 6, the plurality of the through holes 1aa is linearly provided so as to be aligned in a longitudinal direction of the substrate part 1a, and constitutes a hole row. A plurality of the hole rows are arranged in a lateral direction of the substrate part 1a.

If a display part 1ab for displaying an order to use the drill bits is provided on the surface of the substrate 1a, an operator can select a drill bit to be used for every patient according to the order displayed on the display part 1ab, so that it is preferable. More particularly, the display part 1ab displays an order to use a plurality of drill bits in a series for every diameter of a dental implant fixture. The display part 1ab displays the order to use the plurality of drill bits in a series for every diameter of the dental implant fixture, and is provided on the surface of the substrate part 1a by, for example, sticking a seal having a hole on the drill bit displaying portion. Further, if a section display part 1ac for sectioning and displaying locations in which the instruments other than the drill bits are inserted is provided on the surface of the substrate part 1a, the operator can easily select the instruments other than the drill bits at a glance, so that it is preferable. The section display part 1ac sections and displays portions in which the instruments other than the drill bits are inserted, like the display part 1ab, and is provided on the surface of the substrate part 1a by, for example, sticking a seal having a hole on the sectioning and displaying portion. In addition, in the example illustrated in FIG. 1, the display part 1ab and the section display part 1ac are provided on the surface of the substrate part 1a by sticking a seal on which the drill bit displaying portion and the sectioning and displaying portion are displayed.

Figure 6:
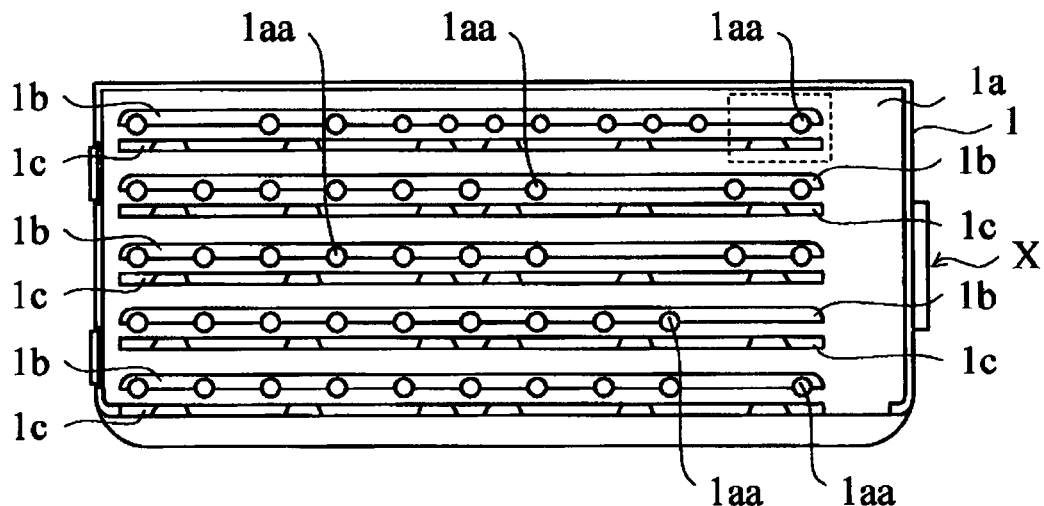
FIG. 6 is a bottom view illustrating an example of a tray main body.
Figure 7:
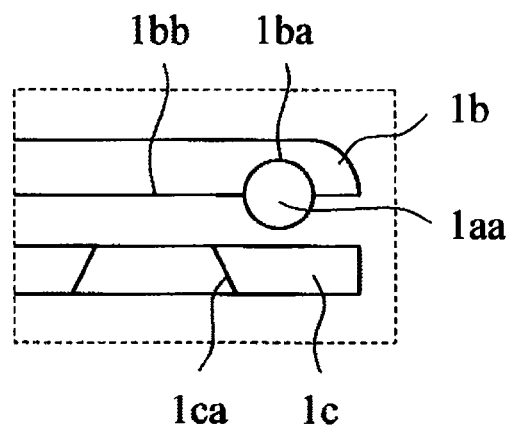
FIG. 7 is an enlarged view of a portion sectioned with a dotted line of the tray main body in FIG. 5.

The holding plates 1b are portions for clamping and holding the drill bits and the instruments other than drill bits, which are inserted into the through holes 1aa respectively, together with the holding members 2 described below, and are erected from a back surface of the substrate part 1a along each of hole rows. The holding plate 1b basically has a flat plate shape, for example, as illustrated in FIGS. 6 and 7. However, the holding plate 1b includes half circular cylindrical recessed parts 1ba at portions corresponding to each of through holes 1aa for clamping and holding the drill bits and the instruments other than drill bits, which are inserted into the through holes 1aa respectively, together with the holding member 2.

The holding member supporting plates 1c are portions for detachably clamping and attaching the holding member 2 together with the holding plates 1b, and are erected respectively having a fixed interval with respect to a plane 1bb along the half circular cylindrical recessed part 1ba side of the holding plate 1b. In addition, if the holding member supporting part 1c includes a plurality of fitting cutout parts 1ca, for example, as illustrated in FIGS. 6 and 7, the holding member 2 can be held without causing a positional shift.

Figure 8:
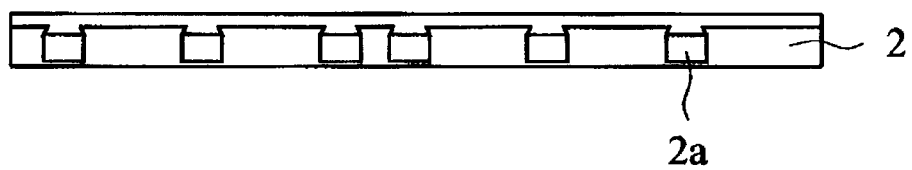
FIG. 8 is a perspective view illustrating an example of a holding member.

The holding members 2 are members for clamping and holding the drill bits and the instruments other than the drill bits, which are inserted into through hole 1aa respectively, together with the half circular cylindrical recessed parts 1ba of the holding plates 1b. The holding members 2 are detachably clamped and attached between the holding plates 1b and the holding member supporting plates 1c, which are erected along the hole rows of the substrate part 1a. Further, the holding member 2 is made of an elastic member capable of autoclave sterilizing, such as a rubber or the like, so that the holding member 2 can be subjected to the autoclave sterilizing treatment. In addition, for example, as illustrated in FIG. 8, if a projection part for fitting 2a is provided for fitting to each fitting cutout part 1ca of the holding member supporting plate 1c, the holding member 2 can be held without causing a positional shift.

Figure 2:
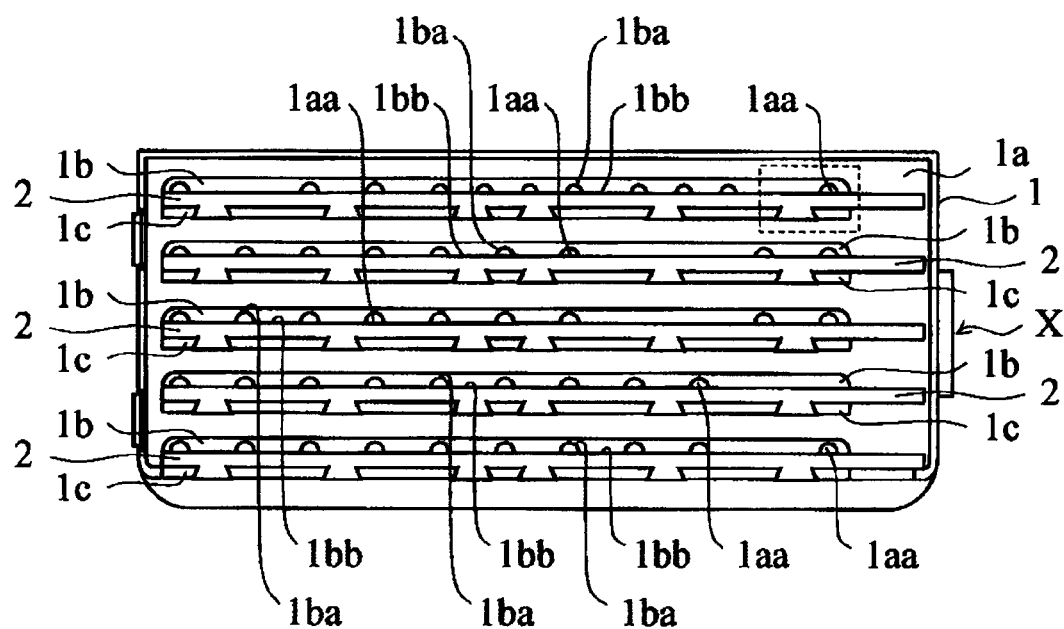
FIG. 2 is a bottom view of the holding tray in FIG. 1.
Figure 3:
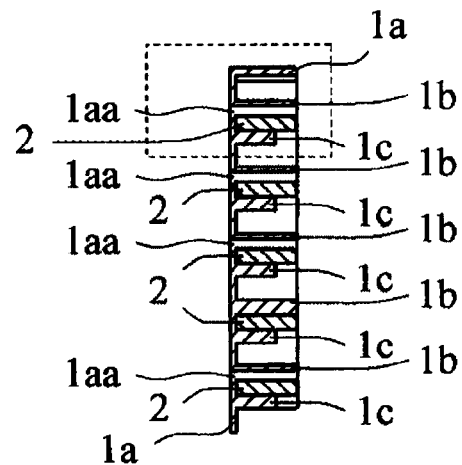
FIG. 3 is a sectional view taken along a Z-Z' line of the holding tray in FIG. 1.
Figure 4:
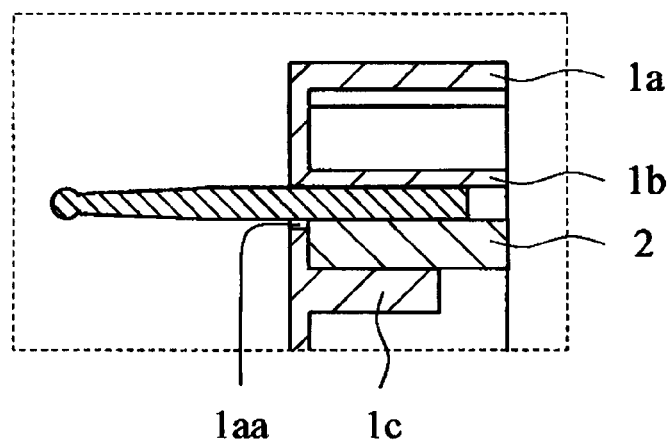
FIG. 4 is an enlarged view illustrating a state that a guide drill bit is inserted into a portion sectioned with a dotted line of the holding tray in FIG. 3.
Figure 5:
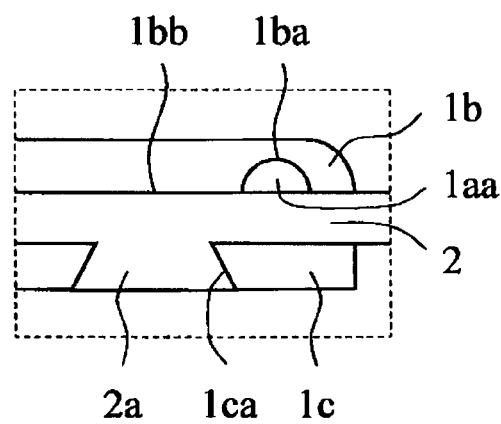
FIG. 5 is an enlarged view of a portion sectioned with a dotted line of the holding tray in FIG. 2.

In the holding tray X having the aforementioned configuration, when each of the drill bits and the instruments other than the drill bits are respectively inserted into the through holes 1aa, each of the drill bits and the instruments other than the drill bits are clamped and held between the half circular cylindrical recessed parts 1ba of the holding plate 1b and the holding member 2, for example, as illustrated in FIG. 4. Thus, each of the drill bits and the instruments other than the drill bits can be inserted and held in the through holes 1aa respectively so as to have a state of being easily taken out at a time of use. Further, a rubber grommet is not fitted to each through hole 1aa, but the holding members 2 are detachably clamped and attached between the holding plates 1b and the holding member supporting plates 1c, which are erected along the hole rows of the substrate part 1a, as illustrated in FIG. 2. Furthermore, the tray main body 1 and the holding member 2 are made of materials capable of autoclave sterilizing. Thus, after using the holding tray X, the holding members 2 and the tray main body 1 can be easily washed by only taking out the holding members 2 from places between the holding plates 1b of the tray main body 1 and the holding member supporting plates 1c. Furthermore, the autoclave sterilizing treatment can be performed by only attaching the holding members 2 between the holding plates 1b of the tray main body 1 and the holding member supporting plates 1c after the washing operation. Therefore, the washing and sterilizing treatment operations can be performed easily.

Further, if the display part 1ab for displaying an order to use the drill bits is provided on the surface of the substrate part 1a of the tray main body 1, an operator can select a drill bit to be used according to the order displayed on the display part 1ab, so that it is preferable.

Furthermore, if the section display part 1ac for sectioning and displaying locations in which the instruments other than the drill bits are inserted is provided on the surface of the substrate part 1a of the tray main body 1, the operator can easily select the instruments other than the drill bits at a glance, so that it is preferable.

What is claimed is:

1. A holding tray (X) for inserting and holding a plurality of drill bits and instruments other than the drill bits used for every patient at a time of drilling of an embedding hole for a dental implant fixture and following operations after the drilling, the holding tray (X) comprising:
   a tray main body (1) made of a hard material capable of autoclave sterilizing, wherein the tray main body (1) comprises holding plates (1b) and holding member supporting plates (1c) on a back surface of a substrate part (1a) having a plurality of hole rows consisting of a plurality of linearly aligned through holes (1aa) in which each of the drill bits and instruments other than the drill bits are inserted, wherein the holding plates (1b) are erected along the hole rows, have a flat plate shape, and include half circular cylindrical recessed parts (1ba) at portions corresponding to each of the through holes (1aa), and
   wherein the holding member supporting plates (1c) are erected respectively having a fixed interval with respect to a plane (1bb) along the half circular cylindrical recessed part (1ba) side of the holding plate (1b); and
   holding members (2) made of an elastic material capable of autoclave sterilizing, wherein the holding members (2) are detachably clamped and attached between the holding plates (1b) and the holding member supporting plates (1c), and clamp and hold the drill bits and the instruments other than the drill bits inserted into the through holes (1aa) in the hole rows, together with the half circular cylindrical recessed parts (1ba) of the holding plates (1b).

2. The holding tray as claimed in claim 1,
   wherein a display part (1ab) for displaying an order to use drill bits is provided on a surface of the substrate part (1a) of the tray main body (1).

3. The holding tray as claimed in claim 1 or 2,
   wherein a section display part (1ac) for sectioning and displaying locations in which the instruments other than the drill bits are inserted provided on the surface of the substrate part (1a) of the tray main body (1).

* * * * *